(12) United States Patent
Magda et al.

(10) Patent No.: US 6,657,058 B1
(45) Date of Patent: Dec. 2, 2003

(54) METAL FREE TEXAPHYRIN SYNTHESIS

(75) Inventors: Darren Magda, Cupertino, CA (US); Jonathan L. Sessler, Austin, TX (US); Sharon Hannah, Vancouver (CA)

(73) Assignees: Pharmacyclics, Inc., Sunnyvale, CA (US); Board of Regents, University of Texas System, Austin, TX (US)

( * ) Notice: Subject to any disclaimer, the term of this patent is extended or adjusted under 35 U.S.C. 154(b) by 0 days.

(21) Appl. No.: 10/274,776

(22) Filed: Oct. 18, 2002

Related U.S. Application Data
(60) Provisional application No. 60/350,146, filed on Oct. 19, 2001.

(51) Int. Cl.[7] .............................................. C07D 487/16
(52) U.S. Cl. ...................................................... 540/472
(58) Field of Search ......................................... 540/472

(56) References Cited

U.S. PATENT DOCUMENTS 5,587,463 A * 12/1996 Sessler et al. ................. 534/15
5,594,136 A * 1/1997 Sessler et al. ............... 540/472

\* cited by examiner

*Primary Examiner*—Mukund J. Shah
*Assistant Examiner*—Thomas McKenzie
(74) *Attorney, Agent, or Firm*—Vinit G. Kathardekar

(57) ABSTRACT

The present invention provides a process of synthesizing a compound of Formula I

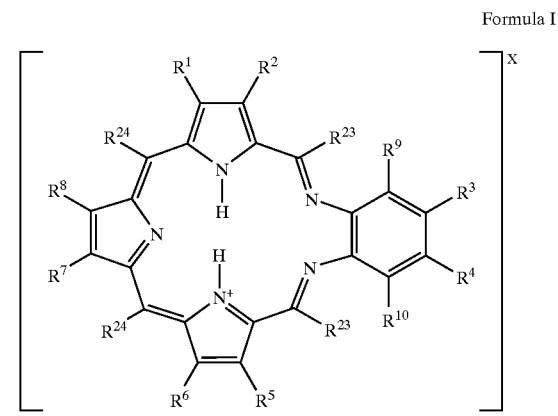

Formula I by treating, in an inert medium and in the presence of an organic base, a compound of formula A

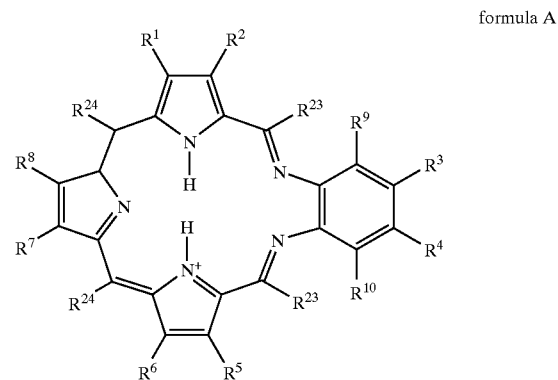

formula A with an organo metallic agent capable of acting as an outer sphere oxidant to form a compound of Formula I.

10 Claims, No Drawings

METAL FREE TEXAPHYRIN SYNTHESIS

CLAIM OF PRIORITY

This application claims priority from U.S. Provisional Application Ser. No. 60/350,146, filed Oct. 19, 2001, the content of which is incorporated herein in its entirety.

FIELD OF INVENTION

The present invention related to the synthesis of a metal-free form of Texaphyrin (compounds of Formula I), an aromatic porphyrin-like macrocycle.

BACKGROUND OF THE INVENTION

The synthesis of the first metal complex of Texaphyrin, an aromatic Schiff-base macrocycle comprised of a tripyrrolyldimethene unit joined to a phenylenediamine through two imine-type linkages, was reported in 1988. This species, an aromatic cadmium(II) complex, was prepared via a simultaneous oxidation-metalation process, that involved treating a reduced non-aromatic porphyrinogen-like precursor, a so-called "sp³-texaphyrin" (named to reflect the hybridization at the bridging carbon atoms) with a Cd(II) salt and air as reported by Jonathan Sessler et al. (see Sessler, J. L., Johnson, M. R. & Lynch, V., *J. Org. Chem.* 1987, v. 52, pp. 4394–4397). Analysis of the metal complex of Texaphyrin showing that it contains a central core that is 20% larger than that of porphyrin, led to the conclusion that this "expanded porphyrin" should coordinate other large cations, including ones that do not fit within the confines of the porphyrin core. This prediction was subsequently realized with nearly the full series of lanthanide(III), as well as Y(III) and In(III), Texaphyrin complexes now being known.

In early work it was reported that the free-base form, Compound of Formula I, of an organic-soluble Texaphyrin was obtained by heating a solution of sp³-texaphyrin and N,N-N',N'-tetramethyl-1,8-naphthalenediamine to reflux while open to air. However, all efforts to reproduce and generalize this result met with failure. As a result, the chemistry and characterization of metal-free texaphyrins has been limited. In this paper, we report an efficient synthesis of this long-sought species.

Keeping the above progress in mind, there is a need for a process that can produce the free base form of an organic-soluble Texaphyrin.

SUMMARY OF THE INVENTION

The present invention provides a process of synthesizing a compound of Formula I

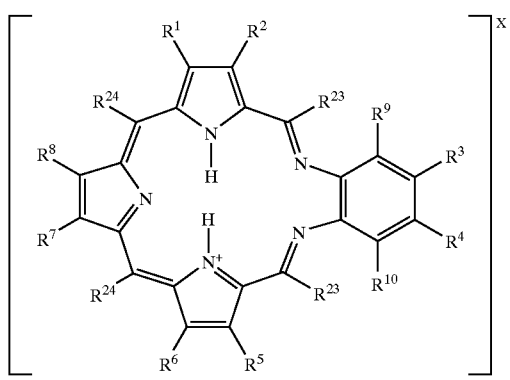

Formula I wherein
$R^1$, $R^2$, $R^3$, $R^4$, $R^5$, $R^6$, $R^7$ and $R^8$ are independently selected from acyl, acyloxy, optionally substituted alkenyl, optionally substituted alkoxy, optionally substituted alkyl, optionally substituted alkynyl, optionally substituted amino, optionally substituted aryl, optionally substituted aryloxy, carboxyl, (optionally substituted alkoxy)carbonyl, (optionally substituted amino)carbonyl, (optionally substituted alkoxy)carbonyloxy, (optionally substituted amino)carbonyloxy, cyano, optionally substituted cycloalkyl, optionally substituted cycloalkenyl, halogen, optionally substituted heteroaryl, optionally substituted heteroaryloxy, optionally substituted heterocyclyl, optionally substituted heterocyclooxy, hydrogen, hydroxyl, nitro, optionally substituted azo, S—$R^{31}$, SO—$R^{31}$, SO$_2$-$R^{31}$, and the moiety X—Y;

$R^9$ and $R^{10}$ are independently selected from H, acyl, acyloxy, optionally substituted alkenyl, optionally substituted alkoxy, optionally substituted alkyl, optionally substituted alkynyl, optionally substituted amino, optionally substituted aryl, optionally substituted aryloxy, carboxyl, (optionally substituted alkoxy)carbonyl, (optionally substituted amino)carbonyl, (optionally substituted alkoxy)carbonyloxy, (optionally substituted amino)carbonyloxy, cyano, optionally substituted cycloalkyl, optionally substituted cycloalkenyl, fluoro, chloro, bromo, optionally substituted heteroaryl, optionally substituted heteroaryloxy, optionally substituted heterocyclyl, optionally substituted heterocyclooxy, hydrogen, hydroxyl, nitro, optionally substituted azo, sulfanyl, sulfinyl, sulfonyl, and the moiety Y—Z;

$R^{23}$ and $R^{24}$ independently at each occurrence are selected from H, OH, optionally substituted $C_{1-4}$ alkyl, optionally substituted $C_{3-10}$ cycloalkyl, halogen, optionally substituted aryl, optionally substituted heteroaryl, optionally substituted heterocyclyl;

$R^{31}$ represents acyl, optionally substituted alkenyl, optionally substituted alky, optionally substituted alkoxy, optionally substituted alkoxycarbonyl, optionally substituted alkynyl, optionally substituted aminocarbonyl, optionally substituted aryl, carboxy, optionally substituted cycloalkyl, optionally substituted heteroaryl, or optionally substituted heterocyclyl;

X represents a charge balancing species (counter ion) selected from halide, NO$_2$, OCOCH$_3$, PF$_6$, BF$_4$, COO, and SO$_4$;

Y is a covalent bond or a linker; and

Z is a catalytic group, a chemotherapeutic agent or a site-directing group;

said process comprising treating, in an inert medium and in the presence of an organic base, a compound of formula A

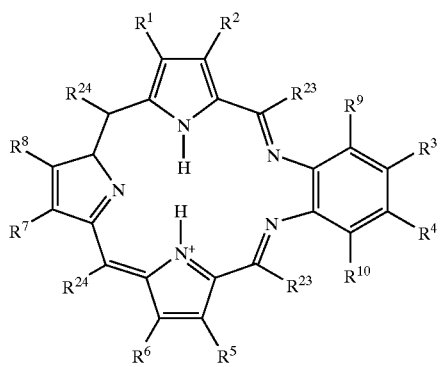

formula A with an organ metallic agent capable of acting as an outer sphere oxidant to form a compound of Formula I.

DETAILED DESCRIPTION

Preferred embodiments of the present invention provide a process wherein the compound of formula A is treated with about 2 to about 8 equivalents of an organo metallic agent, in the presence of a base selected from 2,6-lutidine, collidine, potassium trimethylsilanoate, pyridine triethylamine Hünig's base, 1,8-diazabicyclo[5.4.0] undec-7-ene (DBU), isoquinolinie, piperidine, quinoline, sodium tosylamide, and dimethylaniline.

Another preferred embodiment of the present invention provides a process wherein $R^1$ and $R^6$ are independently selected from H, methyl, $CH_2CH_2OH$, $CH_2CH_2CH_2OH$, and ethyl;

$R^2$ and $R^5$ are independently selected from H, methyl and ethyl;

$R^3$ and $R^4$ are independently selected from H, $OCH_3$, $OC_2H_5$, and $O(CH_2CH_2O)_3CH_3$;

$R^7$ and $R^8$ are independently selected from H, methyl and ethyl;

$R^9$, $R^{10}$, $R^{23}$ and $R^{24}$ independently at each occurrence are selected from H, methyl, ethyl, propyl, alkynyl, alkenyl, halogen, and aryl; and X represents $[PF_6]$.

Provided in yet another preferred embodiment is a process wherein the inert medium is selected from THF, acetonitrile, methylene chloride, DMF, benzene, toluene, chloroform, dichloroethane, and diethyl ether, with THF and acetonitrile being particularly preferred. Yet another preferred embodiment provides a process wherein a compound of formula A is treated with about 3 to about 6 equivalents of an organo metallic agent capable of acting as an outer sphere oxidant, in the presence of from about 1 to about 20 equivalents of 2,6-lutidine.

A further preferred embodiment of the present invention provides a process of synthesizing a compound of Formula I

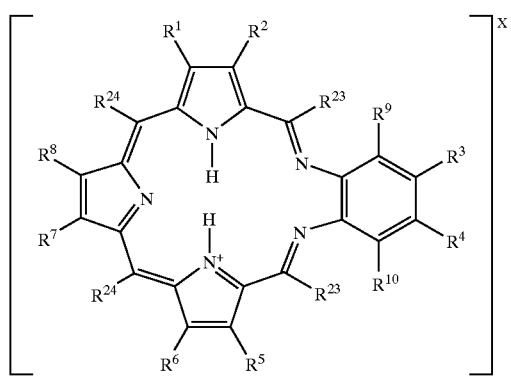

Formula I wherein $R^1$, $R^2$, $R^3$, $R^4$, $R^5$, $R^6$, $R^7$, $R^8$, $R^9$ and $R^{10}$ are independently selected from H, ethyl, methyl, methoxy, methyl, $CH_2CH_2OH$, $CH_2CH_2CH_2OH$, $O(CH_2CH_2O)_3CH_3$, and butyl;

$R^9$, $R^{10}$, $R^{23}$ and $R^{24}$ independently at each occurrence are selected from H, methyl, ethyl, propyl, alkynyl, alkenyl, halogen, and aryl; and X represents $[PF_6]$;

said process comprising treating one equivalent of a compound of formula A, dissolved in acetonitrile,

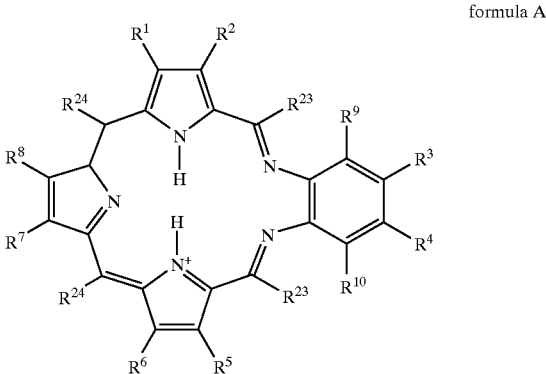

formula A with about 4 to 5 equivalents of an organ metallic agent capable of acting as an outer sphere oxidant selected from the complex ions and salts selected from $[Cp_2Fe]^+$, $[Co(III)(bipyridine)_3]^{3+}$, $[Co(III)(phenanthroline)_3]^{3+}$, $[Co(III)(edta)]^-$, $[Fe(III)(phenanthroline)_3]^{3+}$, and $[Ru(III)(bipyridine)_3]^{3+}$, in the presence of from about 5 to about 10 equivalents of 2,6-lutidine to form a compound of Formula I.

A further preferred process on one where $R^1$ represents ethyl; $R^2$ represents methyl; $R^3$ and $R^4$ represent methoxy; $R^5$ represents methyl; $R^6$ represents ethyl; $R^7$ represents ethyl; $R^8$ represents ethyl; $R^9$, $R^{10}$, $R^{23}$ and $R^{24}$ independently at each occurrence are selected from H, methyl, ethyl, propyl, alkynyl, alkenyl, halogen, and aryl; X represents $[PF_6]$; the organo metallic agent capable of acting as an outer sphere oxidant is ferrocenium hexafluorophasphate.

Another preferred embodiment provides a process wherein $R^1$ represents $CH_2CH_2OH$ or $CH_2CH_2CH_2OH$; $R^2$ represents methyl; $R^3$ and $R^4$ represent $O(CH_2CH_2O)_3CH_3$; $R^5$ represents methyl; $R^6$ represents $CH_2CH_2CH_2OH$; $R^7$ represents ethyl; $R^8$ represents ethyl; $R^9$, $R^{10}$, $R^{23}$ and $R^{24}$ independently at each occurrence are selected from H and methyl; and X represents $[PF_6]$.

EXPERIMENTAL

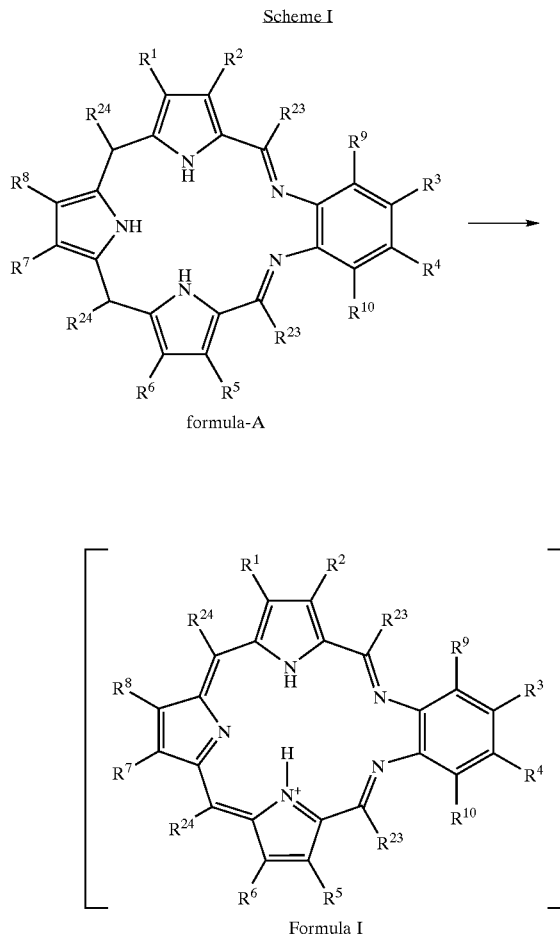

X=charge balancing species.

The process in Scheme I above involves treating a compound of formula-A with an organic metallic agent capable of acting as an outer sphere oxidant, in a neutral medium and in the presence of an organic base, to form a compound of Formula I. The crude compound of Formula I can be purified by techniques known to one skilled in the art, such as column chromatography, recrystallization and the like.

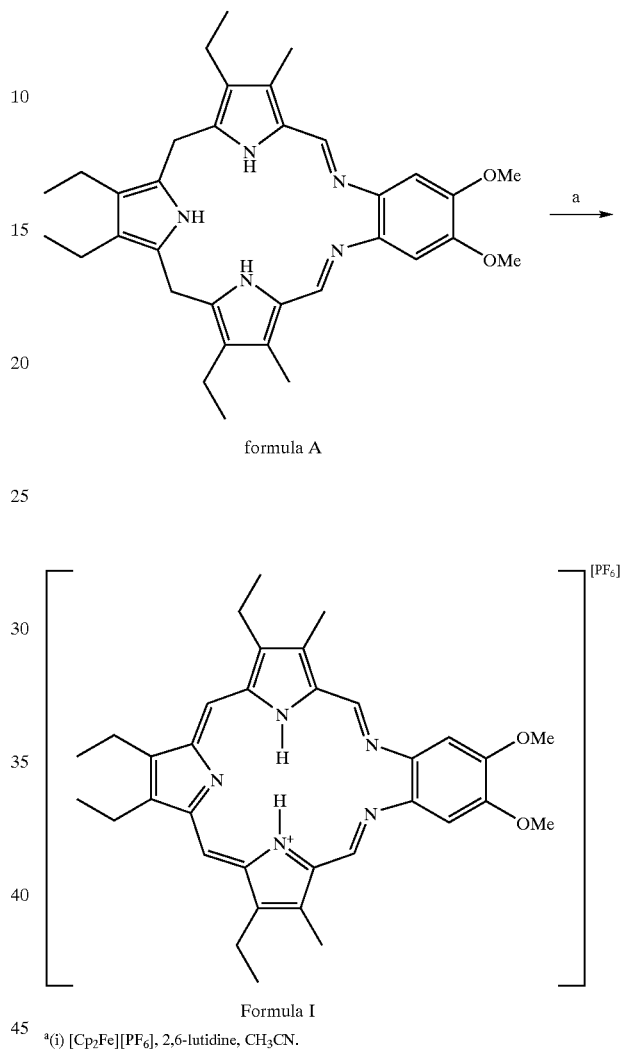

a(i) $[Cp_2Fe][PF_6]$, 2,6-lutidine, $CH_3CN$.

Scheme II illustrates synthesis of a specific compound of formula A. One equivalent of a compound of formula A in acetonitrile (neutral medium) was treated with four equivalents of $[Cp_2Fe][PF_6]$ (an organo metallic agent capable of acting as an outer sphere oxidant), in the presence of about 5 equivalents of 2,6-lutidine (an organic base) in an argon atmosphere to form the compound of Formula I as its $HPF_6$ salt.

The crude product was purified by column chromatography (silica gel; ethyl acetate/dichloromethane, eluent) followed by recrystallization form acetonitrile/diethyl ether to provide the compound of Formula I in a 56% yield.

Definitions:

Outer-sphere electron transfer, as defined in Wilkins, R. G., "Kinetics and Mechanism of Reactions of Transition Metal Complexes," $2^{nd}$ Edition (VCH Publishers, Inc., New York, N.Y., 1991, pp. 258–269), is defined as a reaction in which the ligand spheres or coordination shells of the reactants remain intact (although not completely undisturbed)—there is no bond making or bond breaking and the two reactants do not share at any time a common atom or group. Complexes that can serve as outer-sphere oxidants, under appropriate reaction conditions, are Co(III)(bipyridyl)$_3$, Co(III)(phenanthrolyl)$_3$, Co(III)(edta), Fe(III)(phenanthrolyl)$_3$, Ru(III)(bipyridyl)$_3$.

Halide or halogen represents Cl, Br, I or F.

As used in the present specification, the following words and phrases are generally intended to have the meanings as set forth below, except to the extent that the context in which they are used indicates otherwise.

The term "optional" or "optionally" means that the subsequently described event or circumstance may or may not occur, and that the description includes instances where said event or circumstance occurs and instances in which it does not. For example, "optionally substituted alkyl" means either "alkyl" or "substituted alkyl," as defined below. It will be understood by those skilled in the art with respect to any group containing one or more substituents that such groups are not intended to introduce any substitution or substitution patterns (e.g., substituted alkyl includes optionally substituted cycloalkyl groups, which in turn are defined as including optionally substituted alkyl groups, potentially ad infinitum) that are sterically impractical and/or synthetically non-feasible. Thus, the substituents described for $R^1$ to $R^{12}$ should be generally understood as having a maximum molecular weight of about 1,000 daltons, and more typically, up to about 500 daltons (except in those instances where macromolecular substituents are clearly intended, e.g., polypeptides, polyethylene glycols, DNA, RNA and the like).

The term "acyl" refers to the groups —C(O)—H, —C(O)-(optionally substituted alkyl), —C(O)-(optionally substituted cycloalkyl), —C(O)-(optionally substituted alkenyl), —C(O)-(optionally substituted cycloalkenyl), —C(O)-(optionally substituted aryl), —C(O)-(optionally substituted heteroaryl) and —C(O)-(optionally substituted heterocyclyl).

The term "acyloxy" refers to the moiety —O-acyl, including, for example, —O—C(O)-alkyl.

The term "alkoxy" refers to the groups —O-alkyl, —O-alkenyl, —O-cycloalkyl, —O-cycloalkenyl, and —O-alkynyl. Preferred alkoxy groups are —O-alkyl and include, by way of example, methoxy, ethoxy, n-propoxy, iso-propoxy, n-butoxy, tert-butoxy, sec-butoxy, n-pentoxy, n-hexoxy, 1,2-dimethylbutoxy, and the like.

The term "substituted alkoxy" refers to the groups —O-(substituted alkyl), —O-(substituted alkenyl), —O-(substituted cycloalkyl), —O-(substituted cycloalkenyl), —O-(substituted alkynyl) and —O-(optionally substituted alkylene)-alkoxy. One preferred substituted alkoxy group is "polyalkoxy" or —O-(substituted alkylene)-alkoxy, and includes groups such as —OCH$_2$CH$_2$OCH$_3$, and (or PEG) groups such as —O(CH$_2$CH$_2$O)$_x$CH$_3$, where x is an integer of about 2–20, preferably about 2–10, and more preferably about 2–5. Another preferred substituted alkoxy group is —O-(substituted alkyl), and includes groups such as —OCH$_2$(CH$_2$)$_y$OH, where y is an integer of about 1–10, preferably about 1–4.

The term "alkoxyalkylene" refers to the groups: -alkylene-O-alkyl, -alkylene-O-(substituted alkyl), -(substituted alkylene)-O-alkyl and -(substituted alkylene)-O-(substituted alkyl). A preferred alkoxyalkylene group is -alkylene-O-alkyl and include, by way of example, methoxymethylene (—CH$_2$OCH$_3$), methoxyethylene (—CH$_2$CH$_2$OCH$_3$), n-(iso-propoxy)propylene [—CH$_2$CH$_2$CH$_2$OCH(CH$_3$)$_2$] and the like.

The term "alkenyl" refers to a monoradical of a branched or unbranched unsaturated hydrocarbon group preferably having from 2 to 20 carbon atoms, more preferably 2 to 10 carbon atoms and even more preferably 2 to 6 carbon atoms and having at least 1 and preferably from 1–6 sites of vinyl unsaturation. Preferred alkenyl groups include ethenyl (—CH═CH$_2$), 2-propen-1-yl (—CH$_2$CH═CH$_2$), isopropenyl [—C(CH$_3$)═CH$_2$], and the like.

The term "substituted alkenyl" refers to an alkenyl group in which 1 or more (up to about 5, preferably up to about 3) hydrogen atoms is replaced by a substituent independently selected from the group: ═O, ═S, acyl, acyloxy, optionally substituted alkoxy, optionally substituted amino, optionally substituted aryl, optionally substituted aryloxy, carboxyl, (optionally substituted alkoxy)carbonyl, (optionally substituted amino)carbonyl, (optionally substituted alkoxy)carbonyloxy, (optionally substituted amino)carbonyloxy, cyano, optionally substituted cycloalkyl, halogen, optionally substituted heteroaryl, optionally substituted heteroaryloxy, optionally substituted heterocyclyl, optionally substituted heterocyclooxy, hydroxyl, nitro, optionally substituted phosphine, optionally substituted azo, phosphonato, phosphono, sulfanyl, sulfinyl, and sulfonyl.

The term "alkenylene" refers to a diradical derived from the above-defined monoradical, alkenyl. This term is exemplified by groups such as ethenylene (—CH═CH—), the propenylene isomers (e.g., —CH$_2$CH═CH— and —C(CH$_3$)═CH—) and the like.

The term "substituted alkenylene" refers to a diradical derived from the above-defined monoradical, substituted alkenyl.

The term "alkyl" refers to a monoradical branched or unbranched saturated hydrocarbon chain preferably having from about 1 to 20 carbon atoms, more preferably about 1 to 10 carbon atoms, and even more preferably about 1 to 6 carbon atoms. This term is exemplified by groups such as methyl, ethyl, n-propyl, iso-propyl, n-butyl, iso-butyl, n-hexyl, n-decyl, tetradecyl, and the like.

The term "substituted alkyl" refers to an alkyl group in which 1 or more (up to about 5, preferably up to about 3) hydrogen atoms is replaced by a substituent independently selected from the group: ═O, ═S, acyl, acyloxy, optionally substituted alkoxy, optionally substituted amino, optionally substituted aryl, optionally substituted aryloxy, carboxyl, (optionally substituted alkoxy)carbonyl, (optionally substituted amino)carbonyl, (optionally substituted alkoxy)carbonyloxy, (optionally substituted amino)carbonyloxy, cyano, optionally substituted cycloalkyl, halogen, optionally substituted heteroaryl, optionally substituted heteroaryloxy, optionally substituted heterocyclyl, optionally substituted heterocyclooxy, hydroxyl, nitro, optionally substituted phosphine, phosphonato, phosphono, sulfanyl, sulfinyl, and sulfonyl.

One of the preferred optional substituents for alkyl is hydroxy, exemplified by hydroxyalkyl groups, such as 2-hydroxyethyl, 3-hydroxypropyl, 3-hydroxybutyl, 4-hydroxybutyl, and the like; dihydroxyalkyl groups (glycols), such as 2,3-dihydroxypropyl, 3,4-dihydroxybutyl, 2,4-dihydroxybutyl, and the like; and those compounds known as polyethylene glycols, polypropylene glycols and polybutylene glycols, and the like.

The term "alkylene" refers to a diradical derived from the above-defined monoradical, alkyl. This term is exemplified by groups such as methylene (—CH$_2$—), ethylene (—CH$_2$CH$_2$—), the propylene isomers [e.g., —CH$_2$CH$_2$CH$_2$— and —CH(CH$_3$)CH$_2$—] and the like.

The term "substituted alkylene" refers to a diradical derived from the above-defined monoradical, substituted alkyl. Examples of substituted alkylenes are chloromethylene (—CH(Cl)—), aminoethylene (—CH(NH$_2$)CH$_2$—), methylaminoethylene (—CH(NHMe)CH$_2$—), 2-carboxypropylene isomers (—CH$_2$CH(CO$_2$H)CH$_2$—), ethoxyethylene (CH(OCH$_2$CH$_3$)CH$_2$), 3-oxapentylene (—CH$_2$CH$_2$O—CH$_2$CH$_2$—), N-methyl-3-azapentylene (—CH$_2$CH$_2$N(CH$_3$)CH$_2$CH$_2$—), 3,6,9-trioxaundecylene (2-ethoxy-ethoxy)ethylene (—CH$_2$CH$_2$O—CH$_2$CH$_2$—OCH$_2$CH$_2$—OCH$_2$CH$_2$—), and the like.

The term "alkynyl" refers to a monoradical of an unsaturated hydrocarbon, preferably having from 2 to 20 carbon atoms, more preferably 2 to 10 carbon atoms and even more preferably 2 to 6 carbon atoms and having at least 1 and preferably from 1–6 sites of acetylene (triple bond) unsaturation. Preferred alkynyl groups include ethynyl, (—C≡CH), propargyl (or propynyl, —C≡CCH$_3$), and the like.

The term "substituted alkynyl" refers to an alkynyl group in which 1 or more (up to about 5, preferably up to about 3) hydrogen atoms is replaced by a substituent independently selected from the group: ═O, ═S, acyl, acyloxy, optionally substituted alkoxy, optionally substituted amino, optionally substituted aryl, optionally substituted aryloxy, carboxyl, (optionally substituted alkoxy)carbonyl, (optionally substituted amino)carbonyl, (optionally substituted alkoxy)carbonyloxy, (optionally substituted amino)carbonyloxy, cyano, optionally substituted cycloalkyl, halogen, optionally substituted heteroaryl, optionally substituted heteroaryloxy, optionally substituted heterocyclyl, optionally substituted heterocyclooxy, hydroxyl, nitro, optionally substituted phosphine, optionally substituted azo, phosphonato, phosphono, sulfanyl, sulfinyl, and sulfony.

The term "alkynylene" refers to a diradical derived from the above-defined monoradical, alkynyl. Preferred alkynylene groups include ethynylene (—C≡C—), propargylene (—CH$_2$—C≡C—) and the like.

The term "substituted alkynylene" refers to a diradical derived from the above-defined monoradical, substituted alkynyl.

The term "amino" refers to the group —NH$_2$.

The term "substituted amino" refers to the group —NHR or —NRR where each R is independently selected from the group: acyl, optionally substituted alkenyl, optionally substituted alkyl, optionally substituted alkoxy, optionally substituted alkoxycarbonyl, optionally substituted alkynyl, optionally substituted aminocarbonyl, optionally substituted aryl, carboxy, optionally substituted cycloalkyl, optionally substituted heteroaryl, and optionally substituted heterocyclyl. Preferred amino substituents include optionally substituted alkyl, aryl, optionally substituted alkoxycarbonyl (also referred to as a "carbamate"), optionally substituted aminocarbonyl (also referred to as a urea) and heteroaryl.

The term "aromatic" refers to a cyclic or polycyclic moiety having a conjugated unsaturated (4n+2)π electron system (where n is a positive integer), sometimes referred to as a delocalized π electron system.

The term "aryl" refers to an aromatic cyclic hydrocarbon group of from 6 to 20 carbon atoms having a single ring (e.g., phenyl) or multiple condensed (fused) rings (e.g., naphthyl or anthryl). Preferred aryls include phenyl, naphthyl and the like.

The term "substituted aryl" refers to an aryl group in which 1 or more (up to about 5, preferably up to about 3) hydrogen atoms is replaced by a substituent independently selected from the group: ═O, ═S, acyl, acyloxy, optionally substituted alkoxy, optionally substituted amino, optionally substituted aryl, optionally substituted aryloxy, carboxyl, (optionally substituted alkoxy)carbonyl, (optionally substituted amino)carbonyl, (optionally substituted alkoxy)carbonyloxy, (optionally substituted amino)carbonyloxy, cyano, optionally substituted cycloalkyl, halogen, optionally substituted heteroaryl, optionally substituted heteroaryloxy, optionally substituted heterocyclyl, optionally substituted heterocyclooxy, hydroxyl, nitro, optionally substituted phosphine, optionally substituted azo, phosphonato, phosphono, sulfanyl, sulfinyl, and sulfony (except as otherwise constrained by the definition for the aryl substituent).

The term "aryloxy" refers to, the group —O-aryl.

The term "substituted aryloxy" refers to the group —O-(substituted aryl).

The term "arylalkyl" refers to the moiety "-alkylene-aryl" each having the meaning as defined herein. Such arylalkyl groups are exemplified by benzyl, phenethyl, 3-naphthylpropyl and the like. Arylalkyl moieties also fall within the definition of optionally substituted alkyl, e.g., as a 2-phenyl-n-pentyl moiety.

The term "substituted arylalkyl" refers to the moiety "-(optionally substituted alkylene)-(optionally substituted aryl)", each having the meaning as defined herein, where at least one of the aryl or alkylene groups is substituted, e.g., 4-(N-methyl-pyrrolyl)pentylene.

The term "carbonyl" refers to the di-radical "—C(═O)—", which is also written as "—C(O)—".

The term "(optionally substituted alkoxy)carbonyl" refers to the groups: —C(O)O-(optionally substituted alkyl), —C(O)O-(optionally substituted cycloalkyl), —C(O)O-(optionally substituted alkenyl), and —C(O)O-(optionally substituted alkynyl). These moieties are also referred to as esters.

The term "(optionally substituted amino)carbonyl" refers to the group —C(O)-(optionally substituted amino). This moiety is also referred to as a primary, secondary or tertiary carboxamide.

The term "(optionally substituted alkyl)carbonyloxy" refers to the group —O—C(O)-(optionally substituted alkyl). This moiety is also referred to as a "carbonate."

The term "(optionally substituted amino)carbonyloxy" refers to the group —O—C(O)-(optionally substituted amino). This moiety is also referred to as a "carbamate." The term "carboxy" or "carboxyl" refers to the moiety "—C(O)OH", which is also illustrated as "—COOH".

The term "cycloalkyl" refers to non-aromatic cyclic hydrocarbon groups having about 3 to 40 (preferably about 4 to 15) carbon atoms having a single ring or multiple condensed rings. Such cycloalkyl groups include, by way of example, single ring structures such as cyclopropyl, cyclobutyl, cyclopentyl, cyclooctyl, and the like, or multiple ring structures such as adamantanyl, and the like.

The term "substituted cycloalkyl" refers to a cycloalkyl group in which 1 or more (up to about 5, preferably up to about 3) hydrogen atoms is replaced by a substituent independently selected from the group: ═O, ═S, acyl, acyloxy, optionally substituted alkoxy, optionally substituted amino, optionally substituted aryl, optionally substituted aryloxy, carboxyl, (optionally substituted alkoxy)carbonyl, (optionally substituted amino)carbonyl, (optionally substituted alkoxy)carbonyloxy, (optionally substituted amino)carbonyloxy, cyano, optionally substituted cycloalkyl, halogen, optionally substituted heteroaryl, optionally substituted heteroaryloxy, optionally substituted heterocyclyl, optionally substituted heterocyclooxy, hydroxyl, nitro, optionally substituted phosphine, phosphonato, optionally substituted azo, phosphono, sulfanyl, sulfinyl, and sulfony (except as otherwise constrained by the definition for the cycloalkyl substituent).

The term "cycloalkylene" refers to a diradical derived from the above-defined monoradical, cycloalkyl, and is exemplified by 1,1-cyclopropylene, 1,2-cyclobutylene, 1,4-cyclohexylene and the like.

The term "substituted cycloalkylene" refers to the diradical derived from substituted cycloalkyl as defined above.

The term "halo" or "halogen" refers to fluoro, chloro, bromo and iodo.

The term "heteroaryl" refers to an aromatic cyclic hydrocarbon group having about 1 to 40 (preferably from about 3 to 15) carbon atoms and about 1 to 10 heteroatoms (preferably about 1 to 4 heteroatoms, selected from nitrogen, sulfur, phosphorus, and/or oxygen) within at least one ring. Such heteroaryl groups can have a single ring (e.g., pyridyl or furyl) or multiple condensed rings (e.g., indolizinyl or benzothienyl). Preferred heteroaryls include pyridyl, pyrrolyl and furyl.

The term "substituted heteroaryl" refers to a heteroaryl group in which 1 or more (up to about 5, preferably up to about 3) hydrogen atoms is replaced by a substituent independently selected from the group: =O, =S, acyl, acyloxy, optionally substituted alkoxy, optionally substituted amino, optionally substituted aryl, optionally substituted aryloxy, carboxyl, (optionally substituted alkoxy)carbonyl, (optionally substituted amino)carbonyl, (optionally substituted alkoxy)carbonyloxy, (optionally substituted amino)carbonyloxy, cyano, optionally substituted cycloalkyl, halogen, optionally substituted heteroaryl, optionally substituted heteroaryloxy, optionally substituted heterocyclyl, optionally substituted heterocyclooxy, hydroxyl, nitro, optionally substituted phosphine, optionally substituted azo, phosphonato, phosphono, sulfanyl, sulfinyl, and sulfony (except as otherwise constrained by the definition for the heteroaryl substituent).

The term "heteroaryloxy" refers to the group —O-heteroaryl.

The term "heteroarylene" refers to the diradical group derived from heteroaryl (including substituted heteroaryl), as defined above, and is exemplified by the groups 2,6-pyridylene, 2,4-pyridylene, 1,2-quinolinylene, 1,8-quinolinylene, 1,4-benzofuranylene, 2,5-pyridylene, 2,5-indolylene and the like.

The terms "heterocycle", "heterocyclic" and "heterocyclyl" are interchangeable, and refer to a monoradical, saturated or unsaturated, non-aromatic cyclic hydrocarbon group having from about 3 to about 40 (preferably from about 3 to about 15) carbon atoms wherein one to about 10 carbon atoms are independently replaced hetero atoms selected from nitrogen, sulfur, phosphorus, oxygen, and selenium. In a preferred embodiment about 1 to about 4 carbon atoms are replaced by hetero atoms. Such heterocyclic groups can have a single ring or multiple condensed rings. Illustrative examples of a heterocycle are morpholino, piperidinyl, and the like.

The terms "substituted heterocycle", "substituted heterocyclic" and "substituted heterocyclyl" refer to a heterocyclyl group in which 1 or more (up to about 5, preferably up to about 3) hydrogen atoms is replaced by a substituent independently selected from the group: =O, =S, acyl, acyloxy, optionally substituted alkoxy, optionally substituted amino, optionally substituted aryl, optionally substituted aryloxy, carboxyl, (optionally substituted alkoxy)carbonyl, (optionally substituted amino)carbonyl, (optionally substituted alkoxy)carbonyloxy, (optionally substituted amino) carbonyloxy, cyano, optionally substituted cycloalkyl, halogen, optionally substituted heteroaryl, optionally substituted heteroaryloxy, optionally substituted heterocyclyl, optionally substituted heterocyclooxy, hydroxyl, nitro, optionally substituted phosphine, phosphonato, optionally substituted azo, phosphono, sulfanyl, sulfinyl, and sulfony (except as otherwise constrained by the definition for the heterocyclic substituent).

The term "heterocyclylooxy" refers to the group —O-heterocycle.

The term "heterocyclylene" refers to the diradical group formed from a heterocycle, as defined herein, and is exemplified by the groups 2,6-morpholino, 2,5-morpholino and the like.

The term "linker" as used herein means a covalent connection of a functional group (e.g., a site directing group, a catalytic group or a chemotherapeutic agent) to a metallotexaphyrin or its analogue, and may be, for example, a covalent bond or an alkylene, alkenylene, alkynylene, arylene, ether, PEG moiety, and the like, all of which may be optionally substituted. Examples of reactions to form a covalent link include the reaction between an amine (on either the functional group or the linker precursor) with a carboxylic acid (on the other) to form an amide link. Similar reactions well known in the art are described in standard organic chemistry texts such as J. March, "Advanced Organic Chemistry," $4^{th}$ Edition (Wiley-Interscience, New York, 1992).

The term "macrocycle" as used herein refers to a class of polypyrrolic macrocycles that are capable of forming stable complexes with metals by incorporating a metal (as its cation) within a central binding cavity (core) of the macrocycle, and the anions associated with the metal cation are found above and below the core; these anions are known as apical ligands. This class of macrocycles includes porphyrins, the so-called "expanded porphyrins", and similar structures. Specific examples are porphyrins, porphyrin isomers, porphyrin-like macrocycles, benzophyrins, texaphyrins, alaskaphyrins, sapphyrins, rubyrins, porphycenes, chlorins, benzochlorins, and purpurins.

"Texaphyrin" means an aromatic pentadentate macrocyclic expanded porphyrin, also described as an aromatic benzannulene containing both $18\pi$- and $22\pi$-electron delocalization pathways. Texaphyrins and water-soluble texaphyrins, methods of preparation and various uses have been described in U.S. Pat. Nos. 4,935,498, 5,162,509, 5,252,720, 5,256,399, 5,272,142, 5,292,414, 5,369,101, 5,432,171, 5,439,570, 5,451,576, 5,457,183, 5,475,104, 5,504,205, 5,525,325, 5,559,207, 5,565,552, 5,567,687, 5,569,759, 5,580,543, 5,583,220, 5,587,371, 5,587,463, 5,591,422, 5,594,136, 5,595,726, 5,599,923, 5,599,928, 5,601,802, 5,607,924, 5,622,946, and 5,714,328; PCT publications WO 90/10633, 94/29316, 95/10307, 95/21845, 96/09315, 96/40253, 96/38461, 97/26915, 97/35617, 97/46262, and 98/07733; allowed U.S. patent applications Ser. Nos. 08/458,347, 08/591,318, and 08/914,272; and pending U.S. patent application Ser. Nos. 08/763,451, 08/903,099, 08/946,435, 08/975,090, 08/975,522, 08/988, 336, and 08/975,526; each of which are herein incorporated by reference in their entirety.

What is claimed is:

1. A process of synthesizing a compound of Formula I

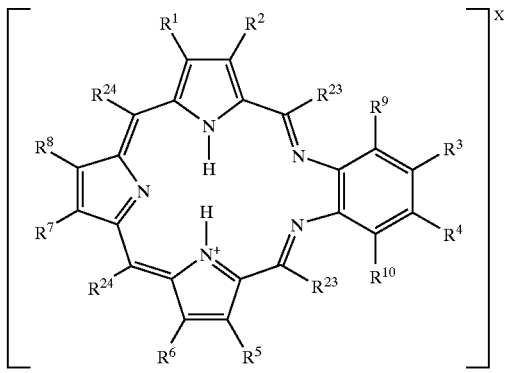

wherein $R^1$, $R^2$, $R^3$, $R^4$, $R^5$, $R^6$, $R^7$ and $R^8$ are independently selected from acyl, acyloxy, optionally substituted alkenyl, optionally substituted alkoxy, optionally substituted alkyl, optionally substituted alkynyl, optionally substituted amino, optionally substituted aryl, optionally substituted aryloxy, carboxyl, (optionally substituted alkoxy)carbonyl, (optionally substituted amino)carbonyl, (optionally substituted alkoxy)carbonyloxy, (optionally substituted amino)carbonyloxy, cyano, optionally substituted cycloalkyl, optionally substituted cycloalkenyl, halogen, optionally substituted heteroaryl, optionally substituted heteroaryloxy, optionally substituted heterocyclyl, optionally substituted heterocyclooxy, hydrogen, hydroxyl, nitro, optionally substituted azo, S—$R^{31}$, SO—$R^{31}$, and $SO_2$—$R^{31}$, $R^9$ and $R^{10}$ are independently selected from H, acyl, acyloxy, optionally substituted alkenyl, optionally substituted alkoxy, optionally substituted alkyl, optionally substituted alkynyl, optionally substituted amino, optionally substituted aryl, optionally substituted aryloxy, carboxyl, (optionally substituted alkoxy)carbonyl, (optionally substituted amino)carbonyl, (optionally substituted alkoxy)carbonyloxy, (optionally substituted amino)carbonyloxy, cyano, optionally substituted cycloalkyl, optionally substituted cycloalkenyl, fluoro, chloro, bromo, optionally substituted heteroaryl, optionally substituted heteroaryloxy, optionally substituted heterocyclyl, optionally substituted heterocyclooxy, hydrogen, hydroxyl, nitro, optionally substituted azo, sulfanyl, sulfinyl, and sulfonyl,;

$R^{23}$ and $R^{24}$ independently at each occurrence are selected from H, OH, optionally substituted $C_{1-4}$ alkyl, optionally substituted $C_{3-10}$ cycloalkyl, halogen, optionally substituted aryl, optionally substituted heteroaryl, optionally substituted heterocyclyl;

$R^{31}$ represents acyl, optionally substituted alkenyl, optionally substituted alky, optionally substituted alkoxy, optionally substituted alkoxycarbonyl, optionally substituted alkynyl, optionally substituted aminocarbonyl, optionally substituted aryl, carboxy, optionally substituted cycloalkyl, optionally substituted heteroaryl, or optionally substituted heterocyclyl; and X represents a charge balancing species (counter ion) selected from halide, $NO_2^{-2}$, —$OCOCH_3$, $PF_6^{-1}$, $BF_4^-$₁, COO-1, and $SO_4^{-2}$—;

said process comprising treating, in an inert medium and in the presence of an organic base, a compound of formula A

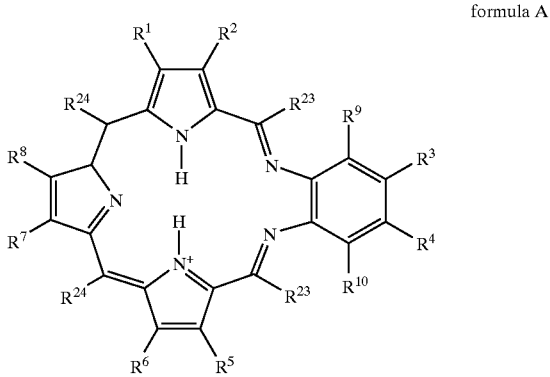

formula A with an organo metallic agent capable of acting as an outer sphere oxidant to form a compound of Formula I.

2. The process of claim 1 wherein the compound of formula A is treated with about 2 to about 8 equivalents of an organo metallic agent, in the presence of a base selected from 2,6-lutidine, collidine, potassium trimethylsilanioate, pyridine, triethylamine, Hünig's base, 1,8-diazabicyclo[5.4.0]undec-7-ene (DBU), isoquinolinie, piperidine, quinoline, sodium tosylamide, and dimethylanliline.

3. The process of claim 2 wherein $R^1$ and $R^6$ are independently selected from H, methyl, $CH_2CH_2OH$, $CH_2CH_2CH_2OH$, and ethyl;

$R^2$ and $R^5$ are independently selected from H, methyl and ethyl;

$R^3$ and $R^4$ are independently selected from H, $OCH_3$, $OC_2H_5$, and $O(CH_2CH_2O)_3CH_3$;

$R^7$ and $R^8$ are independently selected from H, methyl and ethyl;

$R^9$, $R^{10}$, $R^{23}$ and $R^{24}$ independently at each occurrence are selected from H, methyl, ethyl, propyl, alkynyl, alkenyl, halogen, and aryl; and X represents $PF_6^{-1}$.

4. The process of claim 3 wherein the inert medium is selected from THF, acetonitrile, methylene chloride, DMF, benzene, toluene, chloroform, dichloroethane, and diethyl ether.

5. The process of claim 4 wherein the inert medium is selected from THF and acetonitrile.

6. The process of claim 5 wherein a compound of formula A is treated with about 3 to about 6 equivalents of an organo metallic agent capable of acting as an outer sphere oxidant, in the presence of from about 1 to about 20 equivalents of 2,6-lutidine.

7. A process of synthesizing a compound of Formula I

Formula I

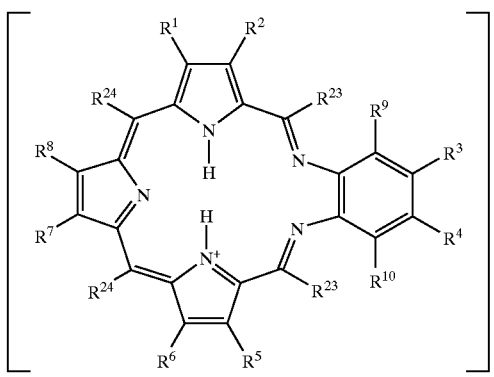

wherein $R^1$, $R^2$, $R^3$, $R^4$, $R^5$, $R^6$, $R^7$, $R^8$, $R^9$ and $R^{10}$ are independently selected from H, ethyl, methyl, methoxy, methyl, $CH_2CH_2OH$, $CH_2CH_2CH_2OH$, $O(CH_2CH_2O)_3CH_3$, and butyl;

$R^9$, $R^{10}$, $R^{23}$ and $R^{24}$ independently at each occurrence are selected from H, methyl, ethyl, propyl, alkynyl, alkenyl, halogen, and aryl; and X represents $[PF_6]$;

said process comprising treating one equivalent of a compound of formula A, dissolved in acetonitrile, formula A

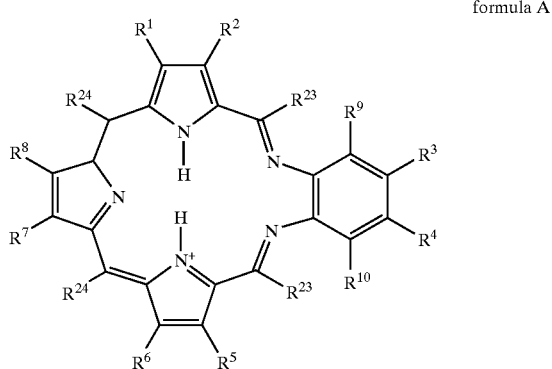

with about 4 to 5 equivalents of an organo metallic agent capable of acting as an outer sphere oxidant selected from the complex ions and salts selected from $[Cp_2Fe]^+$, $[Co(III)(bipyridine)_3]^{3+}$, $[Co(III)(phenanthroline)_3]^{3+}$, $[Co(III)(edta)]^-$, $[Fe(III)(phenanthroline)_3]^{3+}$, and $[Ru(III)(bipyridine)_3]^{3+}$, in the presence of from about 5 to about 10 equivalents of 2,6-lutidine to form a compound of Formula I.

8. The process of claim 7 wherein $R^1$ represents ethyl;

$R^2$ represents methyl;

$R^3$ and $R^4$ represent methoxy;

$R^5$ represents methyl;

$R^6$ represents ethyl;

$R^7$ represents ethyl;

$R^8$ represents ethyl;

$R^9$, $R^{10}$, $R^{23}$ and $R^{24}$ independently at each occurrence are selected from H, methyl, ethyl, propyl, alkynyl, alkenyl, halogen, and aryl; and X represents $PF_6^{-1}$.

9. The process of claim 8 wherein the organ metallic agent capable of acting as an outer sphere oxidant is ferrocenium hexafluorophosphate.

10. The process of claim 9 wherein $R^1$ represents $CH_2CH_2OH$ or $CH_2CH_2CH_2OH$;

$R^2$ represents methyl;

$R^3$ and $R^4$ represent $O(CH_2CH_2O)_3CH_3$;

$R^5$ represents methyl;

$R^6$ represents $CH_2CH_2CH_2OH$;

$R^7$ represents ethyl;

$R^8$ represents ethyl;

$R^9$, $R^{10}$, $R^{23}$ and $R^{24}$ independently at each occurrence are selected from H and methyl; and X represents $PF_6^{-1}$.

* * * * *